US008771162B2

(12) United States Patent  
Lamoureux et al.

(10) Patent No.: US 8,771,162 B2  
(45) Date of Patent: Jul. 8, 2014

(54) SPACERS FOR USE IN BRACHYTHERAPY, RADIOTHERAPY, AND OTHER MEDICAL THERAPY

(75) Inventors: Gary A. Lamoureux, Woodbury, CT (US); Warren Johnston, Thomaston, CT (US); Lino Costantini, Trumbull, CT (US)

(73) Assignee: Eckert & Ziegler Bebig S. A. (BE)

( * ) Notice: Subject to any disclaimer, the term of this patent is extended or adjusted under 35 U.S.C. 154(b) by 333 days.

(21) Appl. No.: 12/963,410

(22) Filed: Dec. 8, 2010

(65) Prior Publication Data

US 2011/0263923 A1     Oct. 27, 2011

Related U.S. Application Data

(60) Provisional application No. 61/327,540, filed on Apr. 23, 2010.

(51) Int. Cl.
*A61M 36/00* (2006.01)

(52) U.S. Cl.
USPC .................................................. 600/7; 600/8

(58) Field of Classification Search
CPC .............. A61N 5/1014; A61N 5/1027; A61N 2005/101; A61N 2005/1008; A61N 2005/1014; A61N 2005/1018; A61N 2005/1019; A61N 2005/1023; A61N 2005/1024
USPC ................................ 600/3, 7, 8; 424/451–502
See application file for complete search history.

(56) References Cited

U.S. PATENT DOCUMENTS

| 6,497,647 | B1* | 12/2002 | Tucker | 600/8 |
| 2003/0144570 | A1* | 7/2003 | Hunter et al. | 600/1 |
| 2005/0113629 | A1* | 5/2005 | Patrick et al. | 600/7 |
| 2005/0250973 | A1* | 11/2005 | Ferguson | 600/8 |
| 2006/0222701 | A1* | 10/2006 | Kulkarni et al. | 424/451 |
| 2007/0021643 | A1* | 1/2007 | Lamoureux et al. | 600/7 |
| 2009/0304756 | A1* | 12/2009 | Dahne et al. | 424/401 |

FOREIGN PATENT DOCUMENTS

WO   WO 2004/026111 A2   4/2004
WO   WO 2009/097408 A1   8/2009

OTHER PUBLICATIONS

"Expose," in The American Heritage Dictionary of the English Language, Fourth Edition (2000). Accessed: Aug. 16, 2013. Available: http://www.thefreedictionary.com/expose.*
European Patent Office, Extended European Search Report for EP 11 16 3551.2, Jul. 29, 2011, 6 pages.

* cited by examiner

*Primary Examiner* — Jacqueline Cheng
*Assistant Examiner* — Kaylee Wilson
(74) *Attorney, Agent, or Firm* — Meyer IP Law Group

(57) ABSTRACT

A spacer for use in brachytherapy, and radiotherapy, is formed of an encapsulating material in a generally cylindrical or elongated shape. Regions are formed within the spacer and retaining therapeutic loads, such as radiation sources and/or pharmaceutical therapeutic loads, and/or any other substances to treat a patient, such as drug liquids, powder or particles (e.g., microparticles or nanoparticles), with the particles or powders combined with binders, such as polyacrylamide, that are selected to gradually disperse the powder or particles at a desired rate. Such regions can be formed at various locations within the spacer, and can have various shapes depending on the particular design and intended usage. The outer surface of the encapsulating material can optionally include one or more fins, ribs or other physical protuberances or features that improve the fixity of the spacer when implanted within a patient's body.

14 Claims, 5 Drawing Sheets

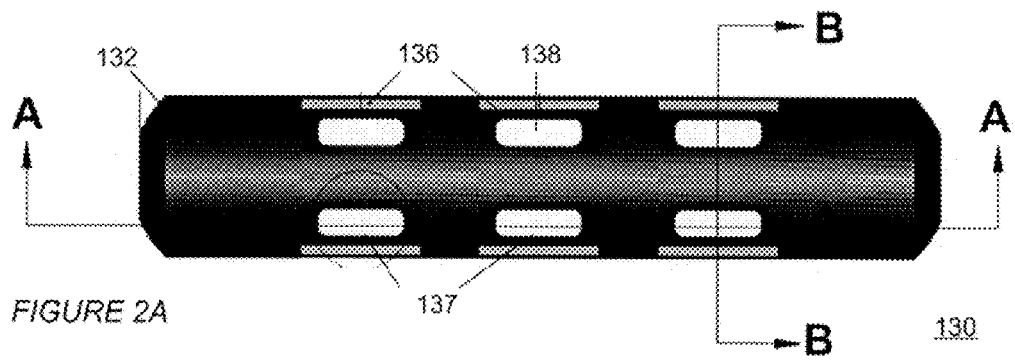
*FIGURE 2A*
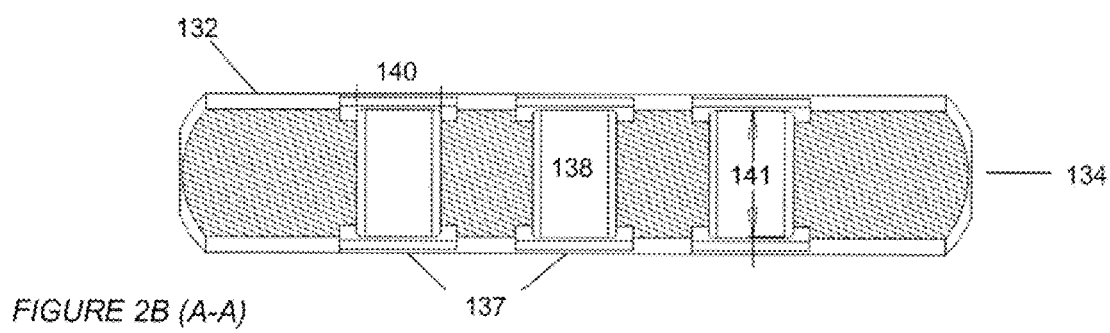
*FIGURE 2B (A-A)*
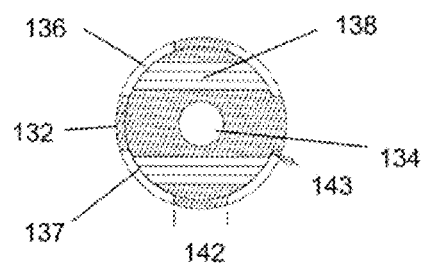
*FIGURE 2C (B-B)*
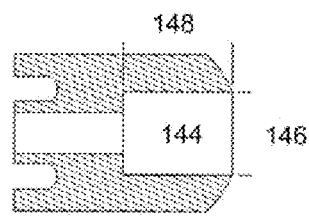
*FIGURE 2D*
*FIGURE 2*

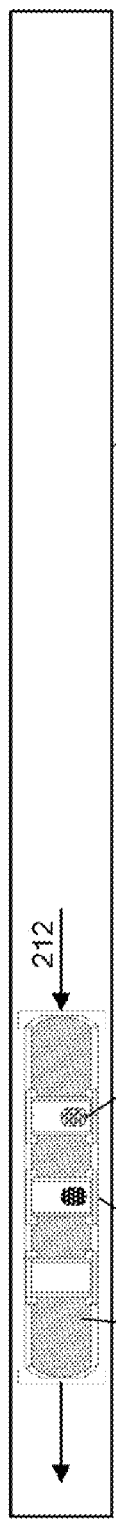
FIGURE 5A
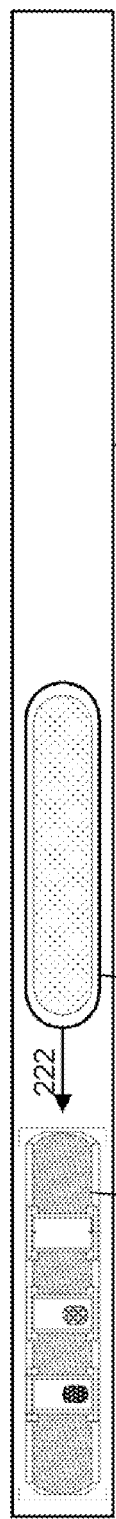
FIGURE 5B
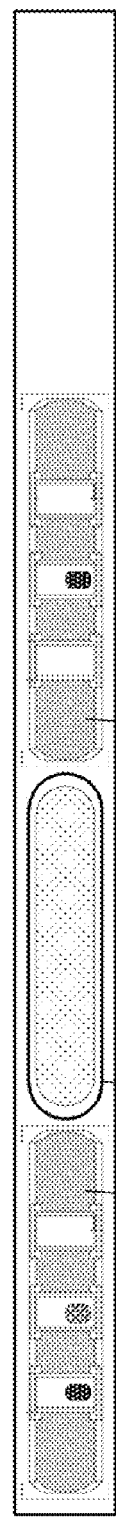
FIGURE 5C
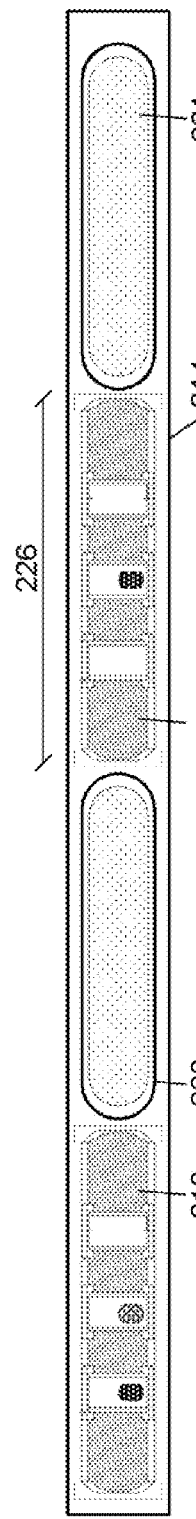
FIGURE 5D
FIGURE 5

SPACERS FOR USE IN BRACHYTHERAPY, RADIOTHERAPY, AND OTHER MEDICAL THERAPY

CLAIM OF PRIORITY

This application claims the benefit of priority to U.S. Provisional Patent Application titled "SPACERS FOR USE IN BRACHYTHERAPY, RADIOTHERAPY, AND OTHER MEDICAL THERAPY", Application No. 61/327,540, filed Apr. 23, 2010; which application is herein incorporated by reference.

CROSS-REFERENCE TO RELATED APPLICATIONS

This application is related to U.S. patent application Ser. No. 11/489,895 (published as U.S. Publication No. US2007/0021642), titled "Devices to Resist Migration and Rotation of Implants Used in Brachytherapy and Other Radiation Therapy"; and U.S. patent application Ser. No. 12/361,285 (published as U.S. Publication No. US2009/0216063), titled "Bio-absorbable Brachytherapy Strands," both of which applications are incorporated by reference herein.

FIELD OF INVENTION

Embodiments of the present invention are generally related to brachytherapy, and are particularly related to therapeutic spacers, for use in implantation and placement of radiation sources or pharmaceutical therapeutic loads.

BACKGROUND

Diseases such as cancer are a leading cause of hospitalizations. In the United States alone, 250,000 men are diagnosed with prostate cancer every year. For the majority of these cases, the disease is localized, and the available treatments include surgery, external beam radiotherapy, and brachytherapy. Approximately 36% of patients choose brachytherapy, which includes the use of radioactive sources or radiation sources placed close to, or within, areas of diseased tissue, and which is particularly beneficial in treating certain types of tumor, such as prostrate cancers.

Temporary brachytherapy is the placement of the radiation source for a short duration, typically several minutes or hours, before being withdrawn. Permanent brachytherapy, also known as seed implantation, is the implanting and positioning of small radioactive seeds in the tumor, positioned or spaced apart from one another using a spacer, and then permanently leaving the seeds within the patient, or until they are gradually absorbed by the body. The use of seeds and similar sources allows a relatively high dose of radiation to be precisely delivered to the treatment site, while minimizing radiation to surrounding healthy tissue. Brachytherapy can be used by itself, or in combination with other therapies, such as surgery or chemotherapy.

Brachytherapy is commonly used in the treatment of prostate cancer, sometimes together with systemic chemotherapy. Currently brachytherapy spacers (elements separating brachytherapy seeds) are smooth, cylindrical segments of bioabsorbable suture material. These spacers were originally made from catgut (ovine or bovine). Currently these spacers are made from bioabsorbable polymers. The spacers function simply as spacing elements to maintain the relative spacing between the treatment seeds, but have little other effect. This is the general area that embodiments of the invention are intended to address.

SUMMARY

Described herein are embodiments of spacers for use in brachytherapy, radiotherapy, and other medical therapy, which can be used to improve a patient's outcome, assist in treating difficult cases and/or combine multiple modalities that are currently performed separately into a single procedure. In accordance with an embodiment, a spacer is formed of an encapsulating material in a generally cylindrical or elongated shape. One or more regions are formed within the spacer for receiving and retaining therapeutic loads, such as radiation sources and/or pharmaceutical therapeutic loads, and/or any other substances that a physician might select to treat a patient, such as drug liquids, powder or particles (e.g., microparticles or nanoparticles), with the particles or powders combined with binders, such as polyacrylamide, that are selected to retain and gradually disperse the powder or particles at a desired rate. The therapeutic agents can also be sprayed onto the spacer or mixed or incorporated into the material of the spacer. The therapeutic agents can, in embodiments, elute from the spacer. Such regions can be formed at various locations within the spacer, and can have various shapes depending on the particular design and intended usage, including, for example, bores, end cavities, wells, ports, slots and/or pockets. The outer surface of the encapsulating material can optionally include one or more fins, ribs or other physical protuberances or features that improve the fixity of the spacer when implanted within a patient's body.

Embodiments of the spacers help to provide proper placement and spacing of any therapeutic agent that is placed in the slots, pockets, grooves, bores, cavities and other recesses provided in the spacer. Also enabled is symmetrical and asymmetrical placement of therapeutic agents in the spacer by providing some selected ones of the slots, pockets, grooves, recesses and the like with certain therapeutic agents. Embodiments of the spacer can be used alone or in combination with brachytherapy seeds in order to deliver therapy loads such as radiation and/or drug therapy loads. When used to provide a distance between brachytherapy radiation seeds, one or more embodiments of the spacers can be placed between seeds. Embodiments of the spacers can be formed in a long strand and then embodiments of individual spacers can be cut or otherwise formed to length from the strand in accordance with a treatment prescription plan. When implanted into the body, the spacer helps provide proper placement and spacing of the radiation brachytherapy seeds or sources.

Therapeutics can include, by way of example only, chemotherapy drug, antibiotic drug, anti-inflammatory drug and Botox type drug. Besides drugs, the wells can be filled with radiation media, contrast media and any other treatment substance including substances for cell marking and photodynamic therapy. Unlike the use of traditional therapies that are either performed separately and/or systemically, embodiments of the present invention allow for combining multiple modalities into a single procedure, such as the precise placement of a chemotherapy drug within the same brachytherapy procedure.

BRIEF DESCRIPTION OF THE DRAWINGS

FIG. 2 (FIGS. 2A-2D) shows an example of a spacer in accordance with a particular embodiment.

FIG. 5 (FIGS. 5A-5D) shows an illustration of the installation and use of a plurality of spacers in accordance with an alternative embodiment.

DETAILED DESCRIPTION

Figure 1:
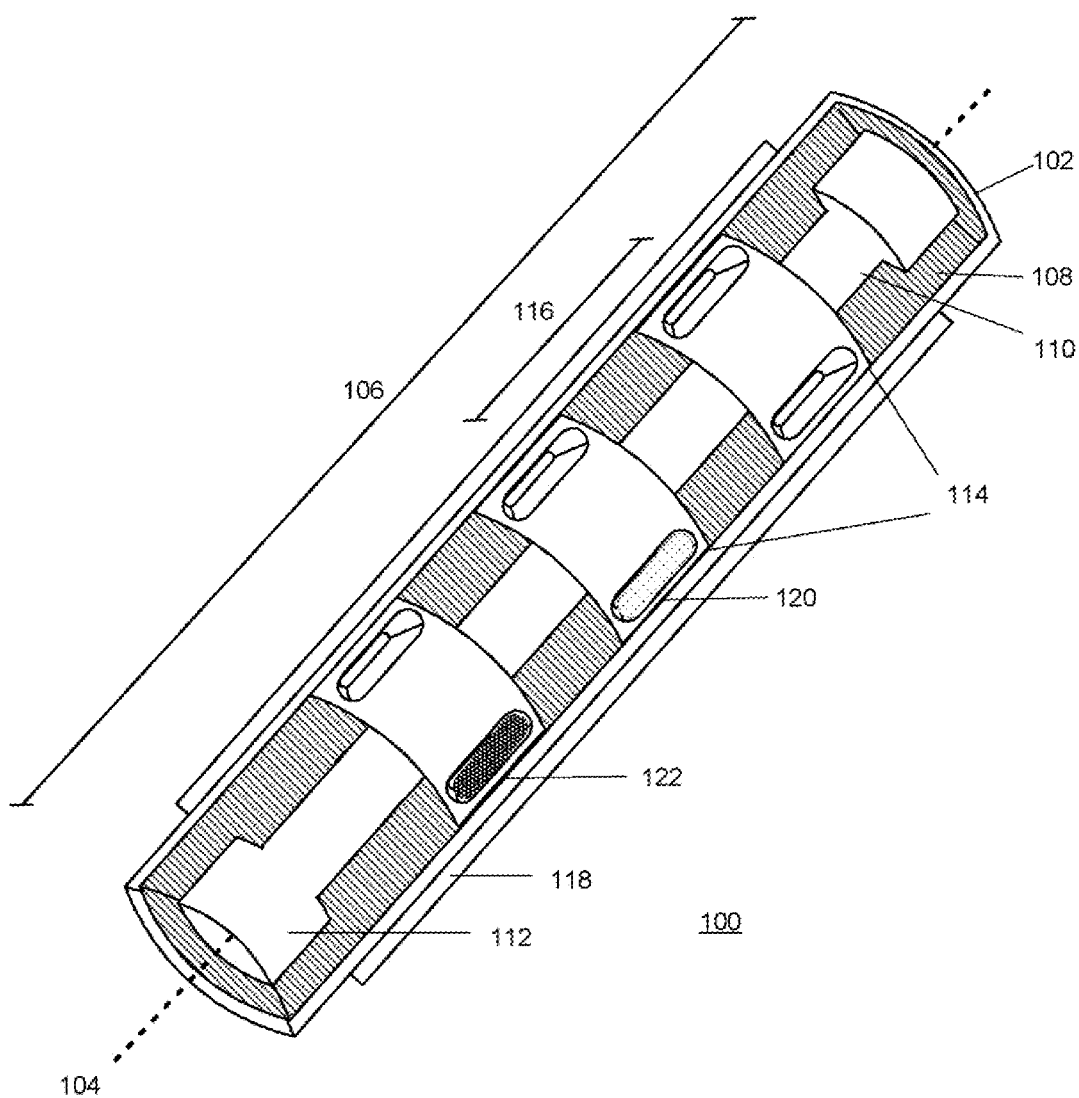
FIG. 1 shows a three-dimensional partial cutaway illustration of an spacer in accordance with an embodiment.

As described above, cancers such as prostate cancer are frequently treated using brachytherapy, of which permanent brachytherapy or seed implantation has shown substantial success. The use of seeds and similar sources allows a relatively high dose of radiation to be precisely delivered to the treatment site, while minimizing radiation to surrounding healthy tissue. However, it can be difficult to treat some cancers with conventional brachytherapy spacers and seeds alone.

Described herein are embodiments of spacers for use in brachytherapy, radiotherapy, and other medical therapy, which can be used to improve a patient's outcome, assist in treating difficult cases and/or combine multiple modalities that are currently performed separately into a single procedure. In accordance with an embodiment, a spacer is formed of an encapsulating material in a generally cylindrical or elongated shape. One or more regions are formed within the spacer for receiving and retaining therapeutic loads, such as radiation sources and/or pharmaceutical therapeutic loads, and/or any other substances that a physician might select to treat a patient, such as drug liquids, powder or particles (e.g., microparticles or nanoparticles), with the particles or powders combined with binders, such as polyacrylamide, that are selected to retain and gradually disperse and elute the powder or particles or therapeutic agent at a desired rate. Such regions can be formed at various locations within the spacer, and can have various shapes depending on the particular design and intended usage, including, for example, bores, end cavities, wells, ports, slots and/or pockets. The outer surface of the encapsulating material can optionally include one or more fins, ribs or other physical protuberances or features that improve the fixity of the spacer when implanted within a patient's body. When implanted into the body, the spacer helps provide proper placement and spacing of radiation seeds and/or sources.

In accordance with an embodiment, a combination of seeds and spacers can reduce or eliminate the need for stranding seeds, and give more flexibility in the filing of custom treatment plans. Embodiments of the current invention provide the ability to anchor the spacer between the seeds.

In accordance with an embodiments, the spacer can be supplied to a customer in a string or rod form (to be subsequently cut to length, in which instance the string can also have cut point indicators to assist in the cutting process), in which the device can be made, for example, with a core of hydrophobic or length stable bioabsorbable polymer with the outer surface or encapsulating layer being made of a hydrophilic bioabsorbable polymer. Accordingly, the device will maintain its cut length, while the outer porous surface can absorb edema to maintain a position in the needle trace for both the spacer and the seed. In accordance with an embodiment the core can be made of a variety of biocompatible materials that are either bioabsorbable or non-bioabsorbable, such as polydioxanone or PDS. Alternatively, the outer hydrophilic and/or bio-absorbable material becomes absorbed in the body and in doing so becomes more securely located in the tissue. As the hydrophilic material becomes absorbed, the remaining hydrophilic material has an irregular surface which is retained in the tissue. Still alternatively, the core hydrophobic material can have an irregular outer surface that is coated with a bio-absorbable and/or hydrophilic material that has a smoother outer surface offering less resistance for initial injection into the tissue. As the bio-absorbable material is absorbed into the tissue, the irregular outer surface of the core engages the tissue and holds the spacer in place. Individual spacers can also be supplied to the customer. In accordance with an embodiment, to use the spacer or similar device for drug elution, the spacer is immersed into a liquid containing the drug, dehydrated and loaded into a brachytherapy needle or similar applicator for implantation, and wherein once implanted into the patient's body, the spacer is rehydrated to cause the drug to elute.

Therapeutics can include chemotherapy drug, antibiotic drug, anti-inflammatory drug and Botox type drug. Besides drugs, the wells can be filled with radiation media, contrast media and any other treatment substance including substances for cell marking and photodynamic therapy.

FIG. 1 shows a three-dimensional partial cutaway illustration of a spacer in accordance with an embodiment. As shown in FIG. 1, in accordance with an embodiment, the spacer 100 is formed of an encapsulating material 102, which forms the overall shape and appearance of the spacer, and which provides supports for any therapeutic loads therein. As indicated herein, the encapsulating material can be a hydrophilic material that can be absorbed into the tissue, which absorption helps retain the spacer in place in tissue. The encapsulating material can cover a core material which is hydrophobic in order to maintain the dimensions of the spacer, for example the length dimension. In accordance with an embodiment, the spacer can have a generally cylindrical or elongated shape about its longitudinal axis 104. The spacer can also have a spacer length 106, which is variable depending on the particular design and intended usage. The interior 108 of the spacer can be formed of, or can contain, either an amount of a similar encapsulating material, a different material, one or more voids, or a combination of material and voids, so that the spacer as a whole has different regions of material and/or voids.

In accordance with an embodiment, one or more regions are formed within the spacer for receiving therapeutic loads. These regions can be the same or different from the voids described above. Such regions can be similarly variable depending on the particular design and intended usage, and can include, for example, a center longitudinal bore 110, one or more end cavities 112, and/or slots or pockets 114.

As used herein, the terms "slots" and "pockets" are used to refer to detents, recesses, cavities or other forms of region which have a similar purpose in receiving therapeutic loads (such as radiation sources or pharmaceutical therapeutic loads, indicated by way of example in FIG. 1 as therapeutic loads 120 and 122 respectively), with the distinction being that pockets are typically considered closed-ended, while slots are typically considered open-ended or otherwise appear as holes extending transversely through the spacer from a first side to an opposite side.

FIG. 1 illustrates an embodiment of a spacer having recesses of the slot type, wherein the slots extend transversely through the spacer from its first dorsal side to its opposite dorsal side. If the slot includes a barrier along its length, then it is more appropriately considered a pocket. Slots and pockets can be separated within the spacer by a slot-separation distance 116, which is similarly variable depending on the particular design and intended usage.

In accordance with an embodiment, the outer surface of the spacer can optionally include one or more fins, ribs or other physical protuberances or features 118. The protuberances can be provided longitudinally around the spacer and/or provided circumferentially around the spacer. Some examples of the type of physical protuberances or features that can be used are described in copending U.S. patent application Ser. No. 11/489,895 (published as U.S. Publication No. 2007/0021642), which application is incorporated by reference herein. Such features improve the fixity of the spacer when placed within the patient's body, since they act to physically reduce the tendency of the spacer to move along, or to rotate about, certain axes.

In accordance with an embodiment, the spacer can be used in treatments such as brachytherapy. For example, one or more of the slots, pockets, indentations, recesses, cavities or similar regions can receive a radiation source (shown by way of example as therapeutic load 120), such as a radiation seed, rod, coil, powder or other form of radiation source. Similarly, one or more of the slots, pockets, detents, recesses, cavities or similar regions can receive a pharmaceutical therapeutic load (shown by way of example as therapeutic load 122), such as a medicine such as a chemotherapy drug. In addition, therapy treatments such as beads (or the contents thereof) that are drug eluding, and that are available from Biocompatibles (UK) can also be used. Others of the slots, pockets, indentations, recesses, cavities or similar regions can be left empty depending on the particular design and intended usage. In this manner, the spacer can be loaded with therapeutic loads, including radiation sources and/or pharmaceutical therapeutic loads, so that when the spacer and its therapeutic loads are ultimately implanted or placed within the patient, along with other spacers and or radiation seeds, the radiation sources and/or pharmaceutical therapeutic loads will remain properly spaced or constrained relative to one another in the spacer and the spacers properly positioned between seeds, and hence with respect to the area being treated.

In accordance with different embodiments, the encapsulating material 102 can be made of a bio-absorbable and/or bio-adherent material, and/or can be formed of a polymeric material or a plastic material and/or non-bioabsorbable material. The fins, ribs or other physical protuberances or features that are used to reduce a tendency of the spacer to move or rotate can be of any number of different shapes and sizes, or combinations thereof, including for example square or rectangular knobs that cause the outer surface of the therapeutic spacer to resemble a knobby tire and/or a plurality of rows which are regularly spaced about the spacer, e.g., with each row extending in a direction that is 90 degrees from the adjacent rows. Alternatively, the protrusions can protrude in a more random or irregular fashion. The above are just a few examples of the possible types of fins, ribs or other physical protuberances or features that can be used. The protrusions can have other dimensions while being within the scope of the present invention, additional examples of which are described in copending U.S. patent application Ser. No. 11/489,895 (published as U.S. Publication No. US2007/0021642).

In accordance with different embodiments, when the radiation seeds 220 (FIG. 5B) or sources, the seeds can be of various types having low energy and low half-life such as Iodine seeds, known as I-125 seeds, including a welded titanium capsule containing iodine 125 adsorbed on a silver rod, or Palladium 103 seeds. Seeds may also have there isotope adsorbed on ceramic beads, resin beads, silver beads, graphite pellets, porous ceramic rods, copper cores, etc. Seeds can have various different shapes, such as, but not limited to, cylindrical with flat ends, cylindrical with rounded (e.g., bullet shaped) and spherical. One of ordinary skill in the art will appreciate from this description that other types of radiation sources and seeds can be used, additional examples of which are similarly described in copending U.S. patent application Ser. Nos. 11/489,895 and 12/361,285 (U.S. Publication Nos. US2007/0021642 and US2009/0216063 respectively).

In accordance with different embodiments, the spacers can be manufactured in various manners. For example, a molding process, such as compression molding or injection molding can be used. A bio-absorbable polymer or some other plastic material is introduced into the mold at a temperature that is above the melt point of the material such that the material flows within the mold cavity. The material is then allowed to set within the mold, e.g., by cooling the mold. After the material has set, the mold is opened, and the finished spacer is retrieved. Therapeutic loads can then be inserted into the cavities, slots and/or pockets as required. Alternatively, solid materials or polymers can be placed in the mold, with the heat from the mold melting the solid materials or polymers in order to form the spacers. Other methods of manufacturing can be used, additional examples of which are similarly described in copending U.S. patent application Ser. Nos. 11/489,895 and 12/361,285 (U.S. Publication Nos. US2007/0021642 and US2009/0216063 respectively).

As part of the molding process, the pockets, slots, and other indentations as well as the central bore and the end cavities can be formed with and defined by elements of the mold. Alternatively, these pockets, slots and other indentations, central bore and end cavities can be formed after the main body of the spacer is molded or otherwise formed. For example, the pockets, slots and other indentation features may be formed using a drilling, etching, or ablating process or by another process that removes material from the spacer.

Further, as part of the manufacturing process, the pockets, slots, indentations, cavities, recesses or other similar regions as well as the end cavities and central bore can be filled with any of the therapeutic agents described therein and other therapeutic agents for treatment of other ailments and diseases for use with the treatment of the prostate or other areas of the body of a human or other mammal or other animal. The therapeutic agents can be loaded into the pockets, slots and other indentations as identified herein with various techniques. Such techniques include coating the spacer the spacer and then removing excess agent, immersing the spacer into the agent, using an inkjet technique, mini-pipette, electro-spinning, auto-dispenser, or other method to inject the therapeutic agent into the pockets, slots or other indentations as identified herein. Spraying techniques can be used to load the pockets, slots or other indentations with the therapeutic agents.

It is also to be understood that any of the therapeutic agents described herein can also be placed in the spacer in such as way as to be evenly or symmetrically distributed in the spacer or distributed in an asymmetrical manner. When distributed in an asymmetrical manner, any of the therapeutic agents can be distributed in order to treat one part of the body or organ of the body and not treat another part of the body or body organ.

In accordance with different embodiments, the radiation sources can be coated with or contain a drug and/or hormone. Alternatively, a drug and/or hormone can be included in the encapsulating material itself, or as a separate therapeutic load. In accordance with an embodiment, the encapsulating material can include, but is not limited to, synthetic polymers and copolymers of glycolide and lactide, polydioxanone and the like. Such polymeric materials are more fully described in U.S. Pat. Nos. 3,565,869, 3,636,956, 4,052,988 and European Patent Publication No. 0030822, and in copending U.S. patent application Ser. Nos. 11/489,895 and 12/361,285 (U.S. Publication Nos. US2007/0021642 and US2009/0216063 respectively), all of which are incorporated herein by reference.

When the spacer has been therapeutic loaded with the required radiation source or pharmaceutical therapeutic loads, it must be implanted within the patient as part of the brachytherapy procedure. In accordance with an embodiment, an applicator such as a MICK™ applicator, or other applicator, can be used to implant the spacers at variable spaced locations within a patient's body. Such an applicator is available from Mick Radio-Nuclear Instruments, Inc., of Mount Vernon, N.Y., and includes a hollow needle that can be inserted into the patient's body, and a magazine for holding and dispensing spacers of the present invention (containing seeds, radiation sources, or other therapeutic loads) as well as, for example, brachytherapy seeds into the needle. The needle can be inserted into a patient in an area where a spacer is to be implanted, and the spacer forced through the needle and into the patient's body. Additional details describing the structure and the use of the MICK applicator are provided in copending U.S. patent application Ser. Nos. 11/489,895 and 12/361,285 (U.S. Publication Nos. US2007/0021642 and US2009/0216063 respectively).

The above-described embodiments of the present invention relate to spacers that include one or more therapy sources. Other embodiments of the invention can be used together with elongated members known as strands that include multiple therapy sources spaced from one another, for example as described in U.S. patent application Ser. No. 10/035,083, and incorporated herein by reference.

FIG. 2 shows an example of a spacer 130 in accordance with a particular embodiment. As shown in FIG. 2A, one example of a spacer can include an encapsulating material 132 formed as described above in the overall shape and appearance of a cylinder or elongated shape about a longitudinal axis, and including a center longitudinal bore 134, and further including a plurality of slot openings or ports 136, 137 on its surface, and, in this example six, slots 138 distributed along the longitudinal axis and extending from a first dorsal side to a second dorsal side. In this embodiment the slots are provided on opposite sides of the central bore.

In accordance with a particular example, the spacer can have a length of 0.189 inch and a diameter of 0.038 inch. Each of the slots can be spaced 0.042 inch apart, beginning 0.052 inch from a first distal end, and can have dimensions of 0.020 inch wide 140, by 0.006 inch high, by 0.030 inch deep 141.

As illustrated in the longitudinal cross-sectional view A-A shown in FIG. 2B, in accordance with this example, the slots 138 extend through the spacer from a first dorsal side to a second dorsal side of the spacer.

As illustrated in the transverse cross-sectional view B-B shown in FIG. 2C, in accordance with this example, a center longitudinal bore 134 is included within the spacer. The linear exterior portions of the spacer 142 can each have a width of 0.012 inch, set 90° apart from one another; while the spacer can have an external diameter of 0.038 inch; and the center bore 134 can have a diameter of 0.010 inch. In accordance with this example, each slot is recessed from the surface of the spacer in a slightly recessed portion, so that the effective minor diameter 143 of the spacer at the slots is 0.034 inch, i.e. somewhat less than that of the spacer as a whole As illustrated in the partial cross-sectional view of the end cavity 144 shown in FIG. 2D, in accordance with this example, the end cavity can be included within the spacer. The center cavity can have a diameter 146 of 0.020 inch, and a length 148 of 0.026 inch.

Figure 3A:
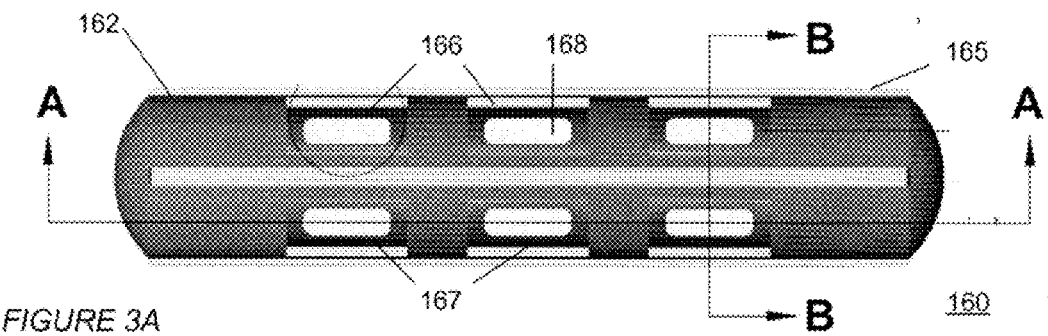
FIG. 3 (FIGS. 3A-3C) shows an example of a spacer in accordance with an alternative embodiment.
Figure 3:
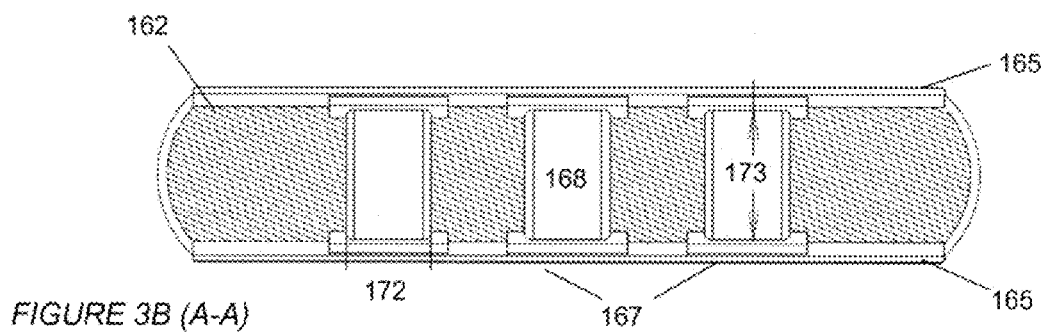
Figure 3:
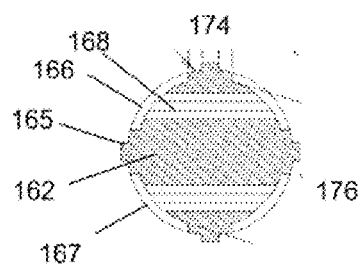

FIG. 3 shows an example of a spacer 160 in accordance with an alternative embodiment. As shown in FIG. 3A, this example of a spacer can similarly include an encapsulating material 162 formed as described above in the overall shape and appearance of a cylinder or elongated shape about a longitudinal axis. In accordance with this embodiment, the spacer does not include a center bore, but does include a plurality of slot openings 166, 167 on its surface, and, in this example six slots 168 distributed along the longitudinal axis and extending from a first dorsal side to a second dorsal side. In accordance with this embodiment, the spacer further includes one or more fins, ribs or other physical protuberances or features 165 that improve the fixity of the spacer when placed in the body. These protuberances can be elongated and provided along the longitudinal length of the spacer and on the outer surface of the spacer. Additionally the protuberances can be provides as rings or ribs that are about perpendicular to the longitudinal axis of the spacer and extend from the surface of the spacer. Combinations of the above protuberances can also be used to ensure the fixity of the spacer in the patient.

In accordance with a particular example, the spacer can have a length of 0.193 inch and a cylindrical diameter of 0.038 inch, with the outer diameter including the fins being 0.041 inch. Each of the slots can be spaced 0.042 inch apart, beginning (measured at its edge) 0.044 inch or (measured at its center) 0.054 inch from a first distal end, and can have dimensions of 0.020 inch wide 140, by 0.006 inch high, by 0.031 inch deep 173.

As illustrated in the longitudinal cross-sectional view A-A shown in FIG. 3B, in accordance with this example, the slots 168 extend through the spacer from a first dorsal side to a second dorsal side of the spacer. In accordance with this example, each slot is positioned at its center 0.011 inch from the central axis, and is recessed from the surface of the spacer in a slightly recessed portion, so that the effective minor diameter 176 of the spacer at the slots is 0.034 inch, i.e. somewhat less than that of the spacer as a whole.

As illustrated in the transverse cross-sectional view B-B shown in FIG. 3C, in accordance with this example, no center bore is included within the spacer. The linear exterior portion of the spacer 174 can have a width of 0.010 inch, and its rib 165 can have a width of 0.004 inch.

Figure 4:
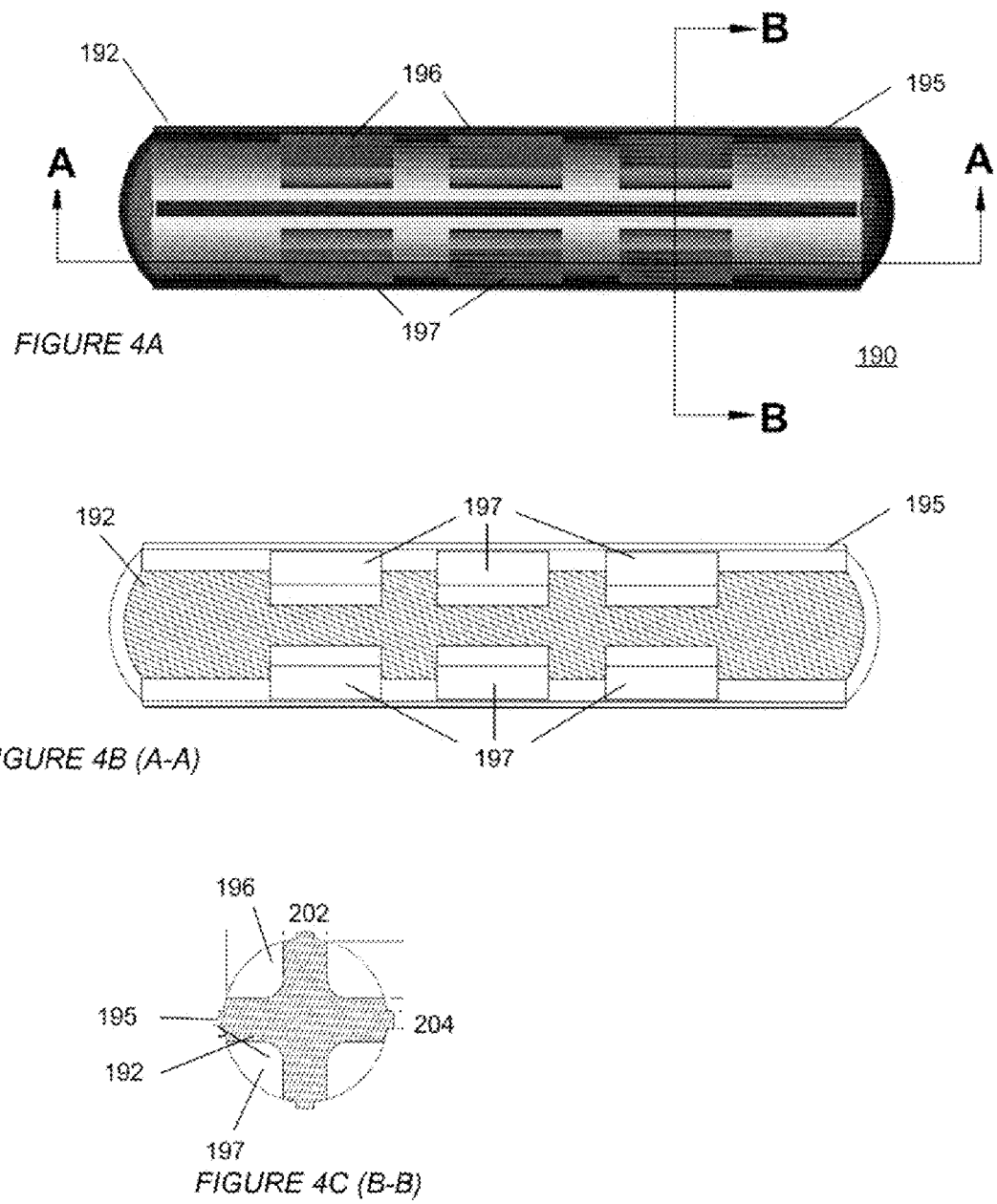
FIG. 4 (FIGS. 4A-4C) shows an example of a spacer in accordance with an alternative embodiment.

FIG. 4 shows an example of a spacer 190 in accordance with an alternative embodiment. As shown in FIG. 4A, this example of a spacer can include an encapsulating material 192 formed as described above in the overall shape and appearance of a cylinder about a longitudinal axis, not in this instance including a center bore or slots, but instead including a plurality of, in this example twelve pockets 196, 197 distributed along the longitudinal axis, and further including fins, ribs or other physical protuberances or features 195 such as longitudinal fins that improve the fixity of the spacer when placed in the body. In accordance with this example, the spacer can have a length of 0.193 inch, and each of the pockets can be spaced 0.042 inch apart, beginning (measured at its center) 0.052 inch from one end, and can have a width of 0.028 inch and a depth of 0.013 inch.

As illustrated in the longitudinal cross-sectional view A-A shown in FIG. 4B, in accordance with this example, the pockets 197 for receiving therapeutic loads do not extend from a first dorsal side to a second dorsal side of the spacer, but are instead close-ended or "pocket-like". In this embodiment the each pocket is located in a quadrant of the spacer.

Thus in this embodiment each quadrant that is located circumferentially about the spacer has a pocket as show in FIG. 4B. In addition along the length of the spacer, each quadrant has three pockets provided therein, as shown in FIG. 4C.

As illustrated in the transverse cross-sectional view B-B shown in FIG. 4C, in accordance with this example, no center bore is included within the spacer. The linear exterior portion of the spacer 202 can have a width of 0.010 inch, and its rib 195 can have a width of 0.004 inch. Further, as seen in FIG. 4C, the pockets are distributed circumferentially about the outer surface of the spacer such that there is one pocket of 0.013×0.013 inch dimension in each quadrant about the circumference of the spacer. Longitudinally along the length of the spacer there are three pockets in each quadrant. With this combination of twelve pockets, drugs can be evenly distributed into all of the pockets or loaded in an asymmetrical way to give a asymmetrical distribution of the therapeutic agent.

FIG. 5 shows an illustration of the therapeutic installation and use of a spacer in accordance with an embodiment. As shown in FIG. 5A, a first spacer 210 is inserted (see arrow) 212 into the patient's body via a channel 214, which can be created using a needle device such as the Mick apparatus. Depending on the particular design and intended usage, the spacer can include therapeutic loads, such as radiation sources and/or pharmaceutical therapeutic loads, indicated by way of example in FIG. 5 as therapeutic loads 216 and 218 respectively. When the spacer and its therapeutic loads are placed within the patient, the radiation sources and/or pharmaceutical therapeutic loads within that particular spacer remain properly spaced relative to one another.

As shown in FIG. 5B, a brachytherapy seed 220 can be inserted (see arrow) 222 into the patient's body via the channel, and abutted next to or adjacent the first spacer 210. When the seed and its therapeutic radiation loads are placed within the patient, the radiation sources and/or pharmaceutical therapeutic loads are properly spaced relative to one another, and also with respect to those of the first spacer 210.

As shown in FIGS. 5C and 5D, the process can be repeated with a subsequent seed 221 or subsequent spacer 224, so that the plurality of radiation sources and/or pharmaceutical therapeutic loads are properly positioned or spaced relative to one another over the plurality of spacers, including spacing the first and second seeds a distance 226 apart, corresponding to the length of the spacer.

The spacers can be provided to the doctors and hospitals in pre-loaded kits along with radiation seeds provide per treatment prescription plan. Alternatively, the spacers can be provided in kits and the doctor or hospital can load the spacers and/or seeds into inserting needles for the medical procedure. Although the above illustrations show the use of similar types of the spacer being used alone, it will be evident to one of ordinary skill in the art that, in other use cases, different types of spacer can be used together, as can different combinations of spacer and seeds be used, to deliver and position the most appropriate combination of radiation sources and/or pharmaceutical therapeutic loads. In accordance with other embodiments different wells, slots, pocket and/or the spacer outer material itself can contain different therapeutic agents.

The foregoing description of the present invention has been provided for the purposes of illustration and description. It is not intended to be exhaustive or to limit the invention to the precise forms disclosed. Many modifications and variations will be apparent to the practitioner skilled in the art.

In particular, while various dimensions, numbers, and positions of slots, pockets and other features have been provided above, in accordance with other embodiments different dimensions, numbers, and positions can be used.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A spacer for treatment of a patient comprising:
    a longitudinal cylindrical body;
    a longitudinal bore through the body;
    a plurality of through slots in the body and about the longitudinal bore of said body, the through slots extending transversely through the body; and
    a therapeutic agent provided in at least some of said through slots.

2. The spacer of claim 1 wherein said through slots each has a center axis and the center axes of said through slots are about perpendicular to the longitudinal bore.

3. The spacer of claim 1 wherein some of the plurality of said through slots are about perpendicular to the longitudinal bore and on one side of the longitudinal bore and some of the plurality of said through slots are about perpendicular to the longitudinal bore and on an opposite side of the longitudinal bore.

4. The spacer of claim 1 including protrusions extending from a surface of the spacer and located at least one of (1) longitudinally along the spacer and spaced from said through slots, (2) circumferentially about said spacer and spaced from said through slots, and (3) both longitudinally along the spacer and spaced from said through slots and circumferentially about said spacer and spaced from said through slots.

5. The apparatus of claim 1, further comprising: an end cavity formed at each end of the body communicating with said longitudinal bore.

6. The apparatus of claim 1, wherein said through slots are about perpendicular to the longitudinal bore.

7. An apparatus for use in brachytherapy, radiotherapy, or other medical therapy or treatment of a patient comprising:
    a spacer formed of one or more materials, and which spacer has a generally cylindrical and elongated shape and a longitudinal axis, and a spacer length associated therewith, and wherein the spacer is adapted to be implanted into a body of the patient; and
    wherein the spacer includes
        a plurality of through slots in the spacer,
        a therapeutic agent provided in at least one of the through slots,
        an outer layer of a hydrophilic material, the hydrophilic material is bio-absorbable, and
        an inner core of a hydrophobic material, the hydrophobic material has an irregular outer surface, and
        wherein when the hydrophilic material is absorbed in tissue, the irregular outer surface of the hydrophobic material is adapted to hold the position of the spacer in the tissue.

8. The apparatus of claim 7, wherein the inner core of the spacer is made of a length stable polymer, which said spacer maintains the spacer length while implanted in a patient, and wherein an outer surface of the spacer is adapted to absorb edema to maintain a position in the needle trace in a patient for both the spacer and a seed.

9. The apparatus of claim 7, wherein the inner core is made of biocompatible materials that are one of bioabsorbable or non-bioabsorbable.

10. The apparatus of claim 7, wherein the outer hydrophilic material can be a bio-absorbable material which is adapted to become absorbed in the body and whereby said spacer becomes more securely located in the tissue of a patient.

11. The apparatus of claim 10, wherein as the hydrophilic material becomes absorbed, the remaining hydrophobic material is exposed with an irregular surface which irregular surface is adapted to be retained in the tissue.

12. The apparatus of claim 10, wherein the core hydrophobic material has an irregular outer surface that is coated with the hydrophilic material of the outer layer that has a smoother outer surface offering less resistance for initial injection into the tissue, and wherein as the hydrophilic material is absorbed into the tissue, the irregular outer surface of the inner core is adapted to engage the tissue and hold the spacer in place.

13. The apparatus of claim 7, wherein, to use the spacer for drug elution, the spacer is immersed into a liquid containing the drug, dehydrated and loaded into an applicator for implantation, and wherein once implanted into the body of the patient, the spacer is rehydrated to cause the drug to elute.

14. The apparatus of claim 7, wherein the spacer includes a spacer surface and a plurality of pockets circumferentially formed in the spacer surface, each of said pockets including an open-end side which is capable of receiving at least one of radiation sources or pharmaceutical therapeutic loads and exposing the at least one of radiation sources or pharmaceutical therapeutic loads to the body, for use in brachytherapy, radiotherapy, and other medical therapy.

* * * * *